(12) United States Patent
Heo et al.

(10) Patent No.: US 11,378,534 B2
(45) Date of Patent: Jul. 5, 2022

(54) METHOD FOR MEASURING CHANGE OF CELL IN REAL TIME AND DEVICE THEREFOR

(71) Applicants: Samsung Electronics Co., Ltd., Suwon-si (KR); Samsung Life Public Welfare Foundation, Seoul (KR)

(72) Inventors: Manseung Heo, Seoul (KR); Eunhyuk Chang, Seoul (KR); Duk L Na, Seoul (KR); Kyusung Lee, Seoul (KR)

(73) Assignees: Samsung Electronics Co., Ltd., Suwon-si (KR); SAMSUNG LIFE PUBLIC WELFARE FOUNDATION, Seoul (KR)

( * ) Notice: Subject to any disclaimer, the term of this patent is extended or adjusted under 35 U.S.C. 154(b) by 681 days.

(21) Appl. No.: 16/346,216

(22) PCT Filed: Oct. 31, 2016

(86) PCT No.: PCT/KR2016/012350
§ 371 (c)(1),
(2) Date: Apr. 30, 2019

(87) PCT Pub. No.: WO2018/079891
PCT Pub. Date: May 3, 2018

(65) Prior Publication Data
US 2020/0049638 A1 Feb. 13, 2020

(51) Int. Cl.
*G01N 27/02* (2006.01)
*G01N 27/12* (2006.01)
(Continued)

(52) U.S. Cl.
CPC ......... *G01N 27/023* (2013.01); *G01N 27/122* (2013.01); *G01N 27/74* (2013.01); *G01N 33/483* (2013.01)

(58) Field of Classification Search
CPC .... G01N 27/023; G01N 27/122; G01N 27/74; G01N 33/483
(Continued)

(56) References Cited

U.S. PATENT DOCUMENTS 7,119,553 B2 * 10/2006 Yang ............... G01R 27/00
702/22
8,808,190 B2 8/2014 Rosell Ferrer et al.
(Continued)

FOREIGN PATENT DOCUMENTS

| CN | 104198449 A | 12/2014 |
|---|---|---|
| CN | 104897730 A | 9/2015 |

(Continued)

OTHER PUBLICATIONS

Zhao et al.; "Experimental study on dielectric relaxation of SiO2 nano-particle suspensions for developing a particle characterization method based on electrical impedance spectroscopy"; Pub. Date May 6, 2015; Powder Technology; 281; 200-213 (Year: 2015).*
(Continued)

*Primary Examiner* — Lee E Rodak
*Assistant Examiner* — Rahul Maini
(74) *Attorney, Agent, or Firm* — NSIP Law

(57) ABSTRACT

Provided are a method and a device capable of: generating a first alternating current magnetic field passing through a chamber having a cell disposed therein, by using a plurality of primary coils arranged on a first plane; receiving a second alternating current magnetic field by using a plurality of secondary coils arranged on a second plane; and measuring an impedance change of a cell by using the first alternating current magnetic field and the second alternating current magnetic field.

21 Claims, 11 Drawing Sheets

(51) Int. Cl.
 G01N 27/74 (2006.01)
 G01N 33/483 (2006.01)

(58) Field of Classification Search
 USPC .......................................................... 324/200
 See application file for complete search history.

(56) References Cited

U.S. PATENT DOCUMENTS

| | | | |
|---|---|---|---|
| 2004/0178790 | A1 | 9/2004 | Gifford et al. |
| 2008/0007275 | A1* | 1/2008 | Rubinsky ............... G01N 22/04 |
| | | | 324/694 |
| 2008/0246472 | A1 | 10/2008 | Igney et al. |
| 2010/0127705 | A1* | 5/2010 | Scharfetter ............ G01V 3/104 |
| | | | 324/318 |
| 2012/0019238 | A1 | 1/2012 | Eichardt et al. |
| 2012/0245436 | A1* | 9/2012 | Rutkove ............... A61B 5/6843 |
| | | | 600/301 |
| 2014/0183970 | A1* | 7/2014 | Kurihara ............ G01R 27/2605 |
| | | | 307/104 |

FOREIGN PATENT DOCUMENTS

| | | |
|---|---|---|
| JP | 2011-013181 A | 1/2011 |
| JP | 2011-089894 A | 5/2011 |
| JP | 2012-002770 A | 1/2012 |
| KR | 10-2009-0099767 A | 9/2009 |
| KR | 10-2012-0006517 A | 1/2012 |
| KR | 10-2014-0058407 A | 5/2014 |

OTHER PUBLICATIONS

International Search Report dated Jul. 11, 2017 in corresponding International Patent Application No. PCT/KR2016/012350 (2 pages in English).

* cited by examiner

METHOD FOR MEASURING CHANGE OF CELL IN REAL TIME AND DEVICE THEREFOR

CROSS REFERENCE TO RELATED APPLICATIONS

This application is a U.S. National Stage Application of International Application No. PCT/KR2016/012350, filed on Oct. 31, 2016, the entire disclosure of which is incorporated herein by reference for all purposes.

TECHNICAL FIELD

The present disclosure relates to methods and devices for measuring a change in a cell in real time.

BACKGROUND ART

Various methods have been proposed to observe the proliferation and change of cells during cell cultures. For example, there is a system for measuring a proliferation degree of a cell by measuring an impedance change value generated during a cell growth using a microelectrode assembly mounted in a chamber. However, because such a system measures a change in impedance inside the chamber using an invasive electrode, the cell may be infected from the outside or damaged by a direct electrical stimulation. Also, high costs may be incurred because the electrode used in such a system is made of a less reactive material such as gold or platinum to maximally prevent cell damage.

In another example, there is a system for measuring the number of cells in a chamber using a light after passing a certain amount of blood through a micro channel. However, such a system has limitations for continuous observation of cells in a certain chamber. Also, cells already used in an experiment are difficult to be reused in the same cell culture environment for other experimental purposes. There is a disadvantage that a special environment such as high-priced equipment capable of measuring minute light and a darkroom is required.

In the case of using techniques of the related art as described above, cells once measured are difficult to be used again for other experiments. However, it may be desirable to perform a different bioassay for the same cell while observing the proliferation and change of cells in real time. Because there is a limit to creation of a new cell of the completely same environment, there is a need for a technique capable of using cells measured once.

DESCRIPTION OF EMBODIMENTS

Technical Problem

Provided are methods and devices for measuring a change in a cell in real time. The technical problem to be solved by the present disclosure is not limited to the above-mentioned technical problem, and other technical problems may be deduced from the following embodiments.

Solution to Problem

According to an aspect of the present disclosure, a device for measuring a change in a cell in real time includes a chamber in which the cell is arranged; an induced magnetic field generator configured to generate a first alternating magnetic field passing through the chamber using a plurality of primary coils arranged on a first plane; an induced magnetic field receiver configured to receive a second alternating magnetic field using a plurality of secondary coils arranged on a second plane; and a controller configured to control the induced magnetic field generator and the induced magnetic field receiver and measure an impedance change of the cell using the first alternating magnetic field and the second alternating magnetic field.

BEST MODE

Figure 1:
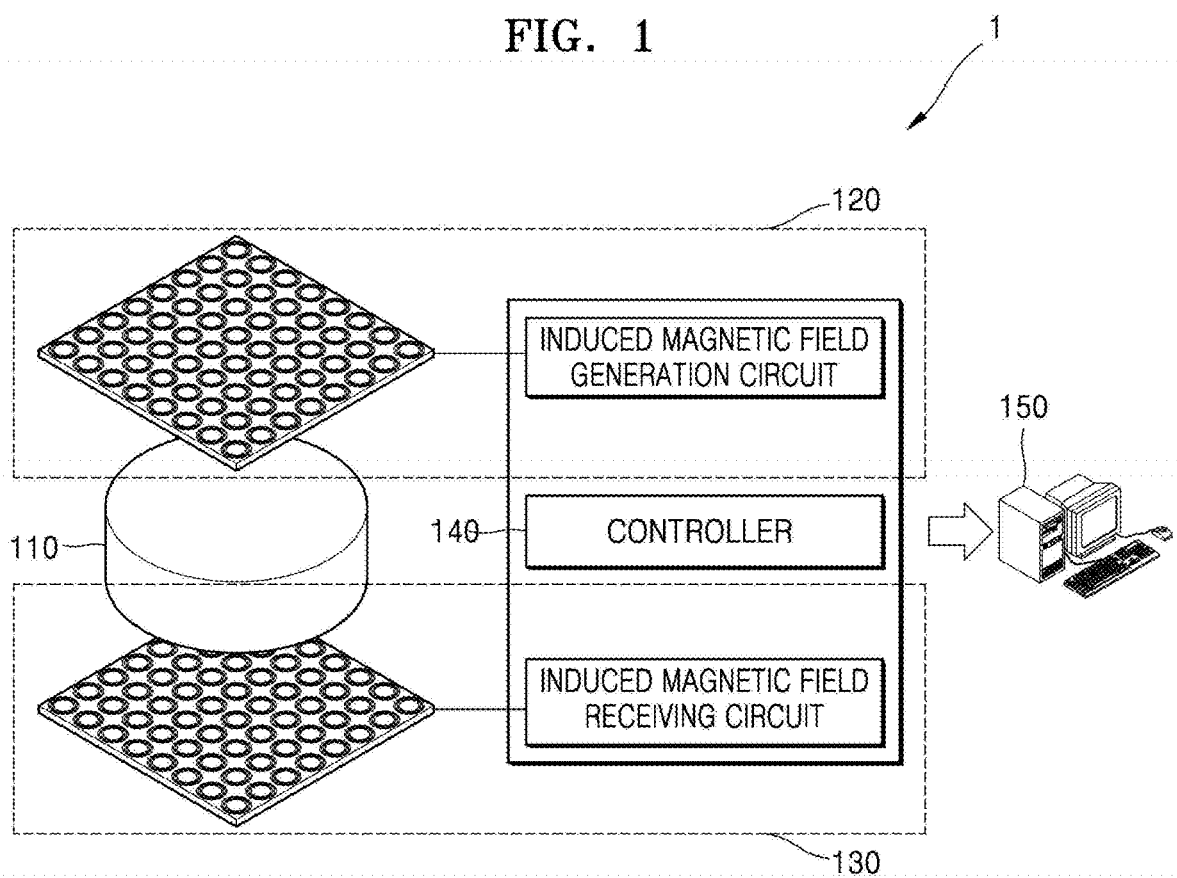
FIG. 1 is a diagram illustrating a system for measuring a change in a cell in real time, according to an embodiment.

A device for measuring a change in a cell in real time includes a chamber in which the cell is arranged; an induced magnetic field generator configured to generate a first alternating magnetic field passing through the chamber using a plurality of primary coils arranged on a first plane; an induced magnetic field receiver configured to receive a second alternating magnetic field using a plurality of secondary coils arranged on a second plane; and a controller configured to control the induced magnetic field generator and the induced magnetic field receiver and measure an impedance change of the cell using the first alternating magnetic field and the second alternating magnetic field, wherein the second alternating magnetic field is a magnetic field obtained by allowing the first alternating magnetic field to pass through the chamber.

The plurality of primary coils may be arranged in an array on the first plane and the plurality of secondary coils are arranged on the second plane parallel to the first plane in the same form as the plurality of primary coils.

The controller may be configured to determine a plurality of coil pairs using the plurality of primary coils and the plurality of secondary coils and individually control an operation of each of the plurality of coil pairs, wherein the plurality of coil pairs include a first coil included in the plurality of primary coils and a second coil among the plurality of secondary coils disposed in a position corresponding to the first coil.

The controller may be configured to sequentially control each of the plurality of coil pairs according to a predetermined time interval.

The controller may be configured to measure the impedance change of the cell while rotating the first plane and the second plane by a predetermined angle.

The controller may be configured to measure the impedance change of the cell by measuring changes in parameters of the first alternating magnetic field and the second alternating magnetic field.

The controller may be configured to measure initial parameters of the first alternating magnetic field and the second alternating magnetic field in a state where the cell is not disposed in the chamber and measure the impedance change of the cell based on the measured initial parameters.

The controller may be configured to measure the impedance change of the cell using at least one of an amplitude, a phase, and a waveform of the first alternating magnetic field and the second alternating magnetic field.

The controller may be configured to determine a change in at least one of a number, a size, and a type of the cell based on the impedance change of the cell.

The induced magnetic field generator may include an inverter configured to convert a direct current (DC) into an alternating current (AC), the plurality of primary coils, and a plurality of switches corresponding to the plurality of primary coils, respectively.

The induced magnetic field receiver may include the plurality of secondary coils, a plurality of switches corresponding to the plurality of secondary coils, respectively, and a rectifier configured to convert alternating current (AC) power into direct current (DC) power.

A method of measuring a change in a cell in real time includes generating a first alternating magnetic field passing through a chamber in which the cell is disposed using a plurality of primary coils arranged on a first plane; receiving a second alternating magnetic field using a plurality of secondary coils arranged on a second plane; and measuring an impedance change of the cell using the first alternating magnetic field and the second alternating magnetic field, wherein the second alternating magnetic field is a magnetic field obtained by allowing the first alternating magnetic field to pass through the chamber.

The plurality of primary coils may be arranged in an array on the first plane and the plurality of secondary coils are arranged on the second plane parallel to the first plane in the same form as the plurality of primary coils.

The method may further include determining a plurality of coil pairs using the plurality of primary coils and the plurality of secondary coils; and individually controlling an operation of each of the plurality of coil pairs, wherein the plurality of coil pairs include a first coil included in the plurality of primary coils and a second coil among the plurality of secondary coils disposed in a position corresponding to the first coil.

The controlling may include sequentially controlling each of the plurality of coil pairs according to a predetermined time interval.

The method may further include measuring the impedance change of the cell while rotating the first plane and the second plane by a predetermined angle.

The method may further include measuring initial parameters of the first alternating magnetic field and the second alternating magnetic field in a state where the cell is not disposed in the chamber and measuring the impedance change of the cell based on the measured initial parameters.

The measuring may include measuring the impedance change of the cell using at least one of an amplitude, a phase, and a waveform of the first alternating magnetic field and the second alternating magnetic field.

The method may further include determining a change in at least one of a number, a size, and a type of the cell based on the impedance change of the cell.

A computer-readable recording medium having recorded thereon one or more programs includes instructions for executing a method of measuring a change in a cell in real time, the method including generating a first alternating magnetic field passing through a chamber in which the cell is disposed using a plurality of primary coils arranged on a first plane; receiving a second alternating magnetic field using a plurality of secondary coils arranged on a second plane; and measuring an impedance change of the cell using the first alternating magnetic field and the second alternating magnetic field.

MODE OF DISCLOSURE

The embodiments will now be described in detail with reference to the accompanying drawings. The following embodiments are intended to illustrate the disclosure and are not intended to limit or limit the scope of the disclosure. It will be understood by those of ordinary skill in the art that various changes in form and details may be made therein without departing from the spirit and scope of the disclosure as defined by the appended claims.

As used herein, the terms 'comprises' or 'comprising' and the like should not be construed as necessarily including all of various elements or operations described in the specification and should be as excluding some of them, or may be interpreted as including additional components or operations.

Also, as used herein, the terms including ordinals such as "first" or "second" may be used to describe various elements, but the elements should not be limited by the terms. The terms are used only for the purpose of distinguishing one element from another. Also, the terms "unit", "module", and the like described in the specification mean units for processing at least one function or operation, which may be implemented in hardware or software or a combination of hardware and software.

The embodiments are directed to a method and a device for measuring a change of a cell in real time, and detailed descriptions thereof will be omitted with respect to matters widely known to one of ordinary skill in the art.

FIG. 1 is a diagram illustrating a system 1 for measuring a change in a cell in real time, according to an embodiment.

Referring to FIG. 1, the system 1 for measuring a change in a cell in real time may include a chamber 110, an induced magnetic field generator 120, an induced magnetic field receiver 130, a controller 140, and an analysis device 150.

The chamber 110 refers to a device including a space in which an object to be measured is located in an experiment. In the chamber 110, the cell to be measured of the system 1 may be arranged. The space in the chamber 110 may be maintained under environmental conditions such as temperature, humidity, light, gas composition, etc., by which the cell may be cultured.

The induced magnetic field generator 120 may be any hardware or electric circuit that generates an induced magnetic field. For example, in order for the induced magnetic field to be generated in a secondary coil included in the induced magnetic field receiver 130, a magnetic flux passing through the secondary coil must be changed. In order to change the magnetic flux passing through the secondary coil, a magnetic field generated by a primary coil included in the induced magnetic field generator 120 must change over time. This means that an alternating current (AC) must flow through the primary coil. Therefore, the induced magnetic field generator 120 may include the primary coil and an inverter, and the inverter may convert a direct current (DC) to AC.

The induced magnetic field receiver 130 may be any hardware or electric circuit that receives the induced magnetic field. For example, the induced magnetic field receiver 130 may include a secondary coil for receiving the induced magnetic field. The reception of the induced magnetic field by the secondary coil may mean that a magnetic field is induced in the secondary coil by a magnetic flux generated by the primary coil. When the magnetic flux passing through the secondary coil changes, an induced current flows in the secondary coil and an induced magnetic field is generated by the induced current flowing in the secondary coil. Because the induced magnetic field is generated by the primary coil, it is expressed that the secondary coil receives the induced magnetic field.

The chamber 110 is located between the primary coil included in the induced magnetic field generator 120 and the secondary coil included in the induced magnetic field receiver 130. An alternating magnetic field generated by the current flowing through the primary coil and an alternating magnetic field generated by the current flowing through the secondary coil may be different from each other. This depends on what is between the primary and secondary coils. The alternating magnetic fields may be affected by the changes in the cell in the chamber 110.

The controller 140 may be implemented by one processor or a plurality of processors. For example, a processor may be implemented as an array of logic gates and may be implemented as a combination of a general purpose microprocessor and a memory in which a program executable in the microprocessor is stored.

The controller 140 plays an overall role for driving and controlling the system 1. For example, the controller 140 may control the induced magnetic field generator 120 and the induced magnetic field receiver 130. Also, the controller 140 may transmit magnetic field change data acquired through the induced magnetic field generator 120 and the induced magnetic field receiver 130 to the analysis device 150.

The analysis device 150 may acquire and analyze the magnetic field change data. The analysis device 150 may measure the change in the cell that occurs during a cell culture based on analysis results. The analysis device 150 may exist independently from the controller 140, as shown in FIG. 1, or may be included in the controller 140.

In the system 1, the alternating magnetic field generated by the induced magnetic field generator 120 may be received through the induced magnetic field receiver 130 after passing through the chamber 110. The system 1 may acquire the magnetic field change data based on the alternating magnetic field generated by the induced magnetic field generator 120 and the alternating magnetic field received by the induced magnetic field receiver 130. Also, the system 1 may measure the change in the cell in the chamber 110 based on the obtained magnetic field change data.

The system 1 may non-invasively measure the change in the cell using the induced magnetic field. Therefore, a possibility that the cell to be measured is damaged is low, and experimental results may be measured more accurately. Also, a once-measured cell may be used for other experiments. The system 1 may also perform a different bioassay for the cell simultaneously with measuring the change such as cell proliferation. The cost for constructing the system 1 is low owing to a simple hardware structure of the induced magnetic field generator 120 and the induced magnetic field receiver 130.

Figure 2:
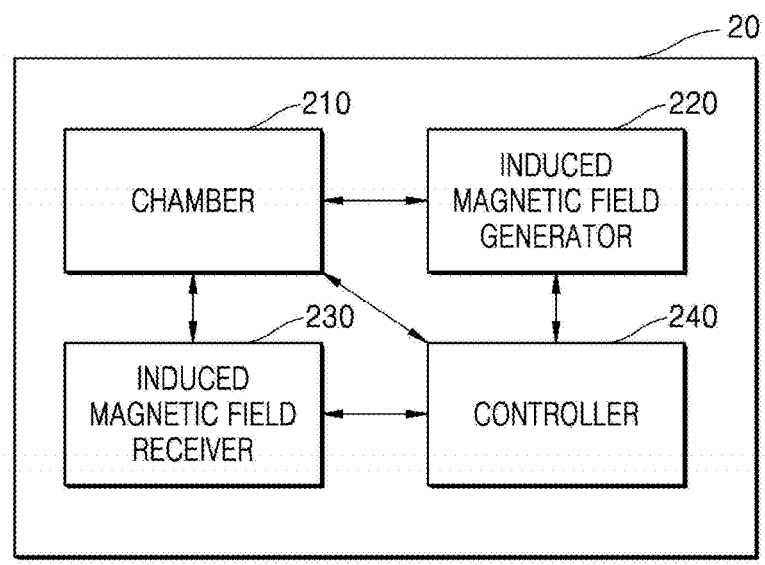
FIG. 2 is a block diagram showing a configuration of a device for measuring a change in a cell in real time, according to an embodiment.

FIG. 2 is a block diagram showing a configuration of a device 20 for measuring a change in a cell in real time, according to an embodiment.

Referring to FIG. 2, the device 20 for measuring the change in the cell in real time may include a chamber 210, an induced magnetic field generator 220, an induced magnetic field receiver 230, and a controller 240.

The chamber 210 means a device including a space in which an object to be measured is located in an experiment. The chamber 210 performs the same function as the chamber 110 of FIG. 1, and thus a redundant description thereof is omitted. In the chamber 210, the cell may be disposed. The cell in the chamber 210 may proliferate and may be measured by other bioassays.

The induced magnetic field generator 220 may be any hardware or electric circuit that receives an induced magnetic field. The induced magnetic field generator 220 performs the same function as the induced magnetic field generator 120 shown in FIG. 1, and thus a redundant description thereof is omitted.

The induced magnetic field generator 220 may generate a first alternating magnetic field passing through the chamber 210 using a plurality of primary coils arranged on a first plane. The induced magnetic field generator 220 may generate an alternating magnetic field by allowing AC to flow through the primary coil. The magnetic field generated by the current flowing in the primary coil is referred to as the first alternating magnetic field. The first alternating magnetic field generated in the induced magnetic field generator 220 may pass through the chamber 210.

The plurality of primary coils may be arranged in an array on the first plane. For example, the plurality of primary coils may be arranged in the form of a one-dimensional or two-dimensional array. When the plurality of primary coils are arranged in the form of a two-dimensional array, the total n×m number of primary coils including n number vertically and m number horizontally may be arranged. Each of the plurality of primary coils may be individually controlled by the controller 240. An arrangement of the plurality of primary coils will be described in detail below with reference to FIG. 3.

The induced magnetic field generator 220 may include an inverter for converting DC into AC, the plurality of primary coils, and a plurality of switches respectively corresponding to the plurality of primary coils. The inverter included in the induced magnetic field generator 220 may convert DC into AC such that the AC flows through the plurality of primary coils. When the AC flows through the plurality of primary coils, the plurality of primary coils may generate an alternating magnetic field.

The controller 240 may individually control each of the plurality of primary coils. The plurality of switches respectively corresponding to the plurality of primary coils may be used to control each of the plurality of primary coils The induced magnetic field receiver 230 may receive a second alternating magnetic field using a plurality of secondary coils arranged on a second plane. The second alternating magnetic field is a magnetic field through which the first alternating magnetic field passes through the chamber 210.

The plurality of secondary coils may be arranged in the same form as the plurality of primary coils on the second plane parallel to the first plane. For example, when the plurality of primary coils are arranged in a two-dimensional array, the plurality of secondary coils may be arranged in the two-dimensional array. When the plurality of primary coils are arranged in an array of n number vertically and m number horizontally, the plurality of secondary coils may also be arranged in the same form.

Because the plurality of primary coils and the plurality of secondary coils are arranged in the same form, a secondary coil at a position corresponding to any of the primary coils may be determined. An arrangement of the plurality of secondary coils will be described in detail below with reference to FIG. 3.

The induced magnetic field receiver 230 may include the plurality of secondary coils, a plurality of switches respectively corresponding to the plurality of secondary coils, and a rectifier for converting AC into DC. The induced magnetic field receiver 230 may receive the second alternating magnetic field using the plurality of secondary coils. The magnetic field induced in the plurality of secondary coils may be the second alternating magnetic field. Each of the plurality of secondary coils may be individually controlled by the controller 240. The plurality of switches respectively corresponding to the plurality of secondary coils may be used to control each of the plurality of secondary coils.

The controller 240 may control the induced magnetic field generator 220 and the induced magnetic field receiver 230. The controller 240 performs the same functions as the controller 140 of FIG. 1, and thus a redundant description thereof is omitted.

The controller 240 may measure an impedance change of the cell using the first alternating magnetic field and the second alternating magnetic field. The controller 240 may acquire change data of the first alternating magnetic field and the second alternating magnetic field and analyze the data to measure the impedance change of the cell.

The controller 240 may measure the impedance change of the cell by measuring changes in parameters of the first alternating magnetic field and the second alternating magnetic field. The controller 240 may measure the impedance change of the cell using at least one of an amplitude, a phase, and a waveform of the first alternating magnetic field and the second alternating magnetic field.

Also, the controller 240 may measure the impedance change of the cell based on AC power transmitted by the first alternating magnetic field and the second alternating magnetic field. The controller 240 may measure a change in a first AC power signal generated in the plurality of primary coils and a change in a second AC power signal induced in the plurality of secondary coils. The controller 240 may measure the impedance change in the cell based on the change of the first AC power signal and the change in the second AC power signal. The change in the first AC power signal and the change in the second AC power signal may be measured based on changes in amplitude, phase and shape, which are parameters of the first AC power signal and the second AC power signal.

The controller 240 may determine a plurality of coil pairs using the plurality of primary coils and the plurality of secondary coils and may individually control an operation of each of the plurality of coil pairs. The coil pairs may include a first coil included in the plurality of primary coils and a second coil among the plurality of secondary coils disposed in a position corresponding to the first coil.

The controller 240 may measure the first alternating magnetic field and the second alternating magnetic field corresponding to each coil pair by individually controlling the coil pairs. Accordingly, the controller 240 may measure the first alternating magnetic field and the second alternating magnetic field in a micro area range corresponding to each coil pair in the chamber 210. The controller 240 may finely measure the impedance change of the cell using the first alternating magnetic field and the second alternating magnetic field measured in the micro area range. The controller 240 may perform a more precise analysis by observing the cell change of a micro part in the chamber 210.

The controller 240 may sequentially control each of the plurality of coil pairs according to a predetermined time interval. For example, it is supposed that the plurality of primary coils and secondary coils are arranged in the form of a two-dimensional array of n number horizontally and m number vertically. When positions of the coils are represented by a matrix, the coil pairs arranged in the two-dimensional array may be represented by the matrix of the total n×m number of $(1, 1), (1, 2), \ldots, (n, m)$. The controller 240 may control the plurality of coil pairs in the order of $(1, 1), (1, 2), \ldots, (n, m)$.

The predetermined time interval may be an arbitrary time interval suitable for measuring the first alternating magnetic field and the second alternating magnetic field corresponding to each coil pair. For example, the predetermined time interval may be a time interval sufficient to measure waveform changes of the first alternating magnetic field and the second alternating magnetic field. The arbitrary time interval may be set by a user or determined by the controller 240.

Also, the controller 240 may measure the impedance change of the cell while rotating the first plane and the second plane by a predetermined angle. The controller 240 may measure the parameter changes of the first alternating magnetic field and the second alternating magnetic field while rotating the first plane and the second plane by a predetermined angle. The controller 240 may measure the impedance change of the cell at various angles using the measured parameter changes of the first alternating magnetic field and the second alternating magnetic field. The controller 240 may measure the change of the cell more stereoscopically by measuring the impedance change of the cell while rotating the first plane and the second plane by the predetermined angle.

The controller 240 may measure initial parameters of the first alternating magnetic field and the second alternating magnetic field when the cell is not disposed in the chamber 210 and measure the impedance change of the cell based on the measured initial parameters. In order to measure the impedance change of the cell using the parameter changes of the first alternating magnetic field and the second alternating magnetic field, the reference of the parameters of the first alternating magnetic field and the second alternating magnetic field may be required. Therefore, the controller 240 may measure the initial parameters of the first alternating magnetic field and the second alternating magnetic field when the cell is not disposed in the chamber 210.

The controller 240 may determine a change in at least one of the number, size, and type of cells based on the impedance change of the cell. In an example, the controller 240 may determine a change in the number of cells based on the impedance change of the cell. For example, when the impedance of the cell measured by the device 20 for measuring the change of the cell in real time gradually decreases, the controller 240 may determine that the number of cells is gradually increasing. In this case, the cells in the chamber 210 may be proliferating.

In another example, the controller 240 may determine a change in the size of the cell based on the impedance change of the cell. For example, when the impedance of the cell measured by the device 20 for measuring the change of the cell in real time decreases gradually, the controller 240 may determine that the size of the cell is gradually increasing. In order for the controller 240 to determine the change in the size of the cell based on the impedance change of the cell, the number of cells to be measured must be maintained to be constant.

In another example, the controller 240 may determine a change in the type of the cell based on the impedance change of the cell. Different types of cells have different impedance distributions. Therefore, when an experiment is performed under the same condition such as the number of cells, the type of the cell may be inferred from the impedance distribution. The controller 240 may determine the type of the cell based on the impedance change of the cell measured using the first alternating magnetic field and the second alternating magnetic field.

Meanwhile, the block diagram of the device 20 for measuring the change of a cell in real time shown in FIG. 2 is a block diagram for an embodiment. Each component of the block diagram may be integrated, added, or omitted according to the specifications of the device 20 for measuring the change of a cell in real time. That is, two or more components may be combined into one component, or one component may be subdivided into two or more components as necessary. Also, a function performed in each block is intended to illustrate embodiments, and the specific operation or device does not limit the scope of the present disclosure.

Figure 3:
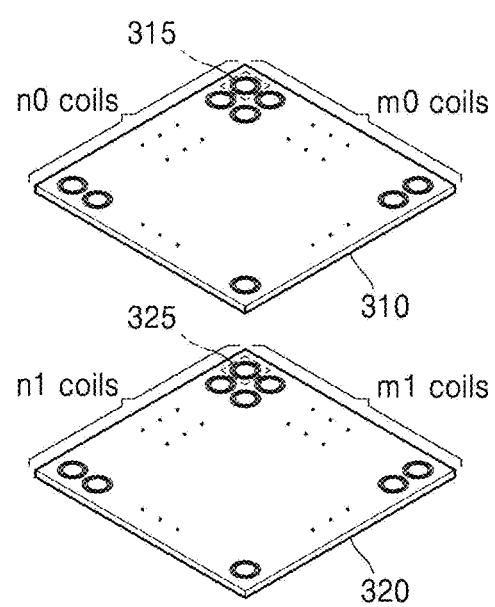
FIG. 3 is a diagram showing a structure of a plurality of primary coils and a plurality of secondary coils according to an embodiment.

FIG. 3 is a diagram showing a structure of a plurality of primary coils and a plurality of secondary coils according to an embodiment.

In order to non-invasively measure a change in a cell, the present embodiment uses an induced magnetic field. Thus, a device for measuring the change in the cell in real time may include the plurality of primary coils and the plurality of secondary coils.

The plurality of primary coils may be arranged in an array on a first plane 310. For example, the plurality of primary coils may be arranged in a two-dimensional array as shown in FIG. 3. The total n×m number of primary coils of n number vertically and m number horizontally may be arranged.

The plurality of secondary coils may be arranged in the same form as the plurality of primary coils on a second plane 320 parallel to the first plane 310. For example, the plurality of secondary coils may be arranged in a two-dimensional array as shown in FIG. 3. The total n×m number of secondary coils of n number vertically and m number horizontally may be arranged. Thus, a secondary coil at a position corresponding to an arbitrary primary coil may be determined.

The device for measuring the change in the cell in real time may determine a plurality of pairs of coils using a plurality of primary coils and a plurality of secondary coils and may individually control an operation of each of the plurality of pairs of coils. The coil pair may include a first coil 315 included in the plurality of primary coils and a second coil 325 of the plurality of secondary coils disposed in a position corresponding to the first coil 315.

For example, when positions of the coils are represented by a matrix, the coil pairs arranged in the two-dimensional array may be represented by the matrix of the total n×m number of (1, 1), (1, 2), . . . , (n, m). Each of the coil pairs corresponding to a (1, 1), (1, 2), . . . , (n, m) may be individually controlled. Therefore, a change in the impedance of the cell may be measured by a micro area unit obtained by dividing the first plane 310 into n×m. By measuring the impedance change of the cell in the micro area unit, the device for measuring the change in the cell in real time may more finely measure the change in the cell in a chamber.

Figure 4:
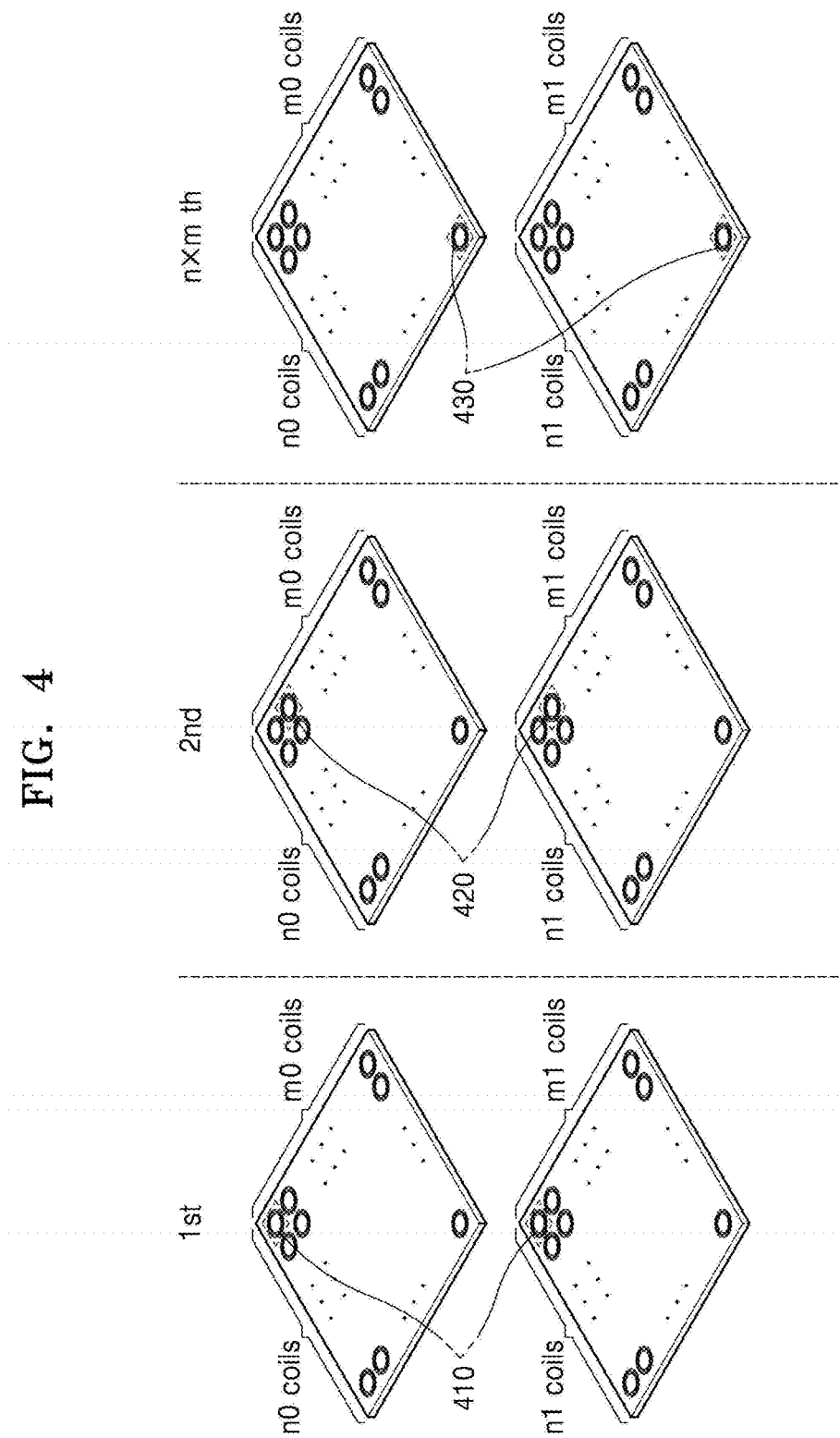
FIG. 4 is a diagram illustrating a method of operating a plurality of pairs of coils, according to an embodiment.

FIG. 4 is a diagram illustrating a method of operating a plurality of pairs of coils, according to an embodiment.

Referring to FIG. 4, n×m coil pairs may be arranged on a first plane and a second plane. Each of the plurality of coil pairs may be sequentially controlled according to a predetermined time interval. For example, as shown in FIG. 4, a coil pair 410 may be firstly controlled. Parameters of a first alternating magnetic field and a second alternating magnetic field at a position corresponding to the coil pair 410 may be measured. Also, a change in a cell at the position corresponding to the coil pair 410 may be measured.

A coil pair 420 may then be controlled. Parameters of the first alternating magnetic field and the second alternating magnetic field at a position corresponding to the coil pair 420 may be measured. Further, a change in the cell at the position corresponding to the coil pair 420 may be measured.

The coil pairs may be then sequentially controlled, and finally a coil pair 430 may be measured at n×m. Parameters of the first alternating magnetic field and the second alternating magnetic field at a position corresponding to the coil pair 430 may be measured. Further, a change in the cell at the position corresponding to the coil pair 430 may be measured. When the change in the cell at the position corresponding to the coil pair 430 is measured, the change in the cell at the position corresponding to the coil pair 410 may be measured again. As described above, the plurality of coil pairs are sequentially controlled, and thus sequential data acquisition may be possible for each micro area.

Figure 5:
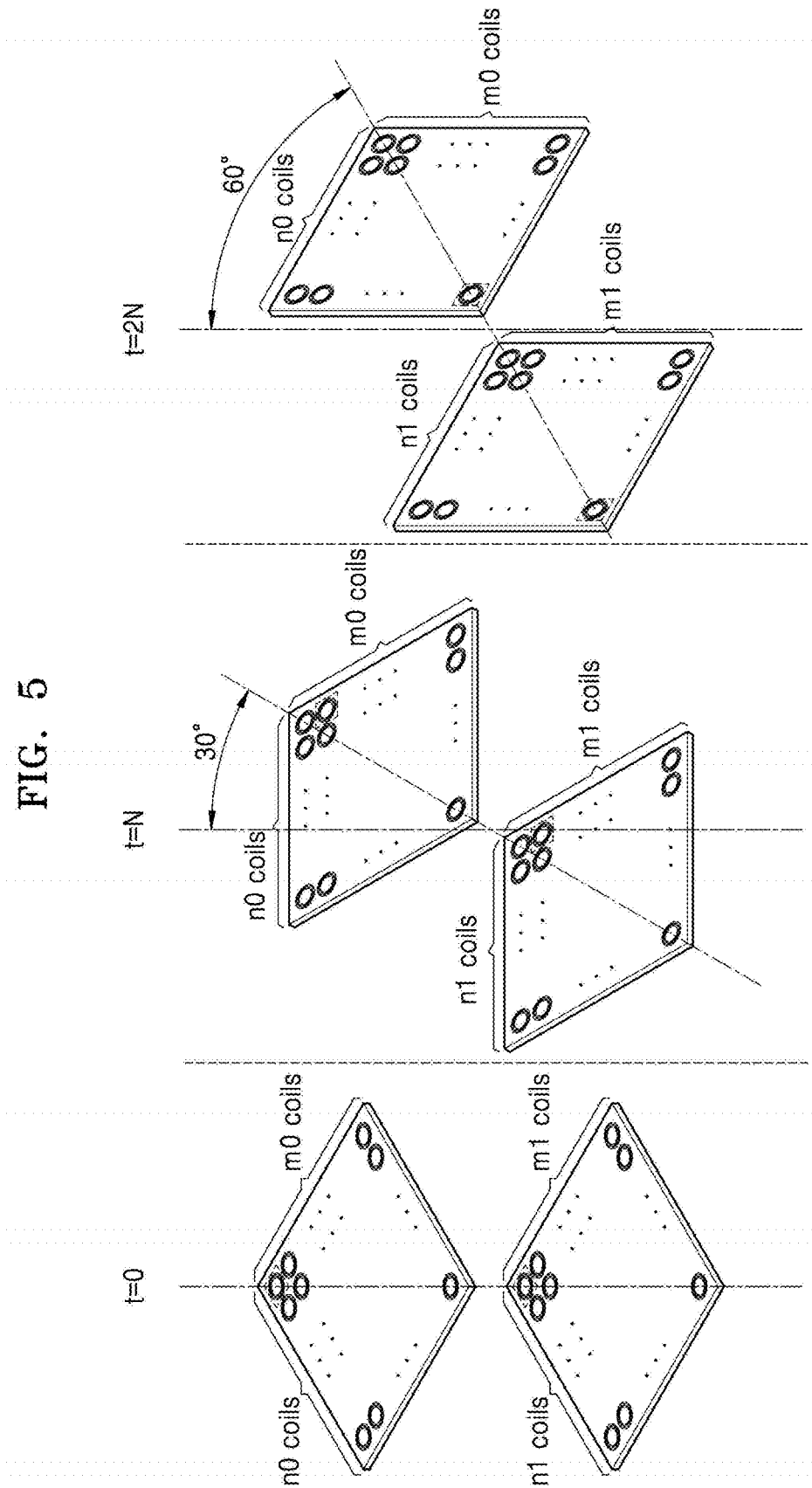
FIG. 5 is a diagram illustrating an example in which a device for measuring a change in a cell in real time measures an impedance change of the cell while rotating a first plane and a second plane by a predetermined angle, according to an embodiment.

FIG. 5 is a diagram illustrating an example in which a device for measuring a change in a cell in real time measures an impedance change of the cell while rotating a first plane and a second plane by a predetermined angle according to an embodiment.

The device for measuring the change in the cell in real time may measure the impedance change of the cell while rotating the first plane and the second plane by the predetermined angle. The device for measuring the change in the cell in real time may measure parameter changes of a first alternating magnetic field and a second alternating magnetic field while rotating the first plane and the second plane by a predetermined angle according to a predetermined time interval.

For example, as shown in FIG. 5, when t=0, the device for measuring the change in the cell in real time may measure the impedance change of the cell without rotating the first plane and the second plane from a certain axis. The device may measure the impedance change of the cell by measuring changes in parameters of the first alternating magnetic field and the second alternating magnetic field.

Next, when t=N, the device may measure the impedance change of the cell after rotating the first plane and the second plane 30 degrees from the certain axis. The device may measure the impedance change of the cell by measuring the parameter changes of the first alternating magnetic field and the second alternating magnetic field.

Subsequently, when t=2N, the device may measure the impedance change of the cell after rotating the first plane and the second plane 60 degrees from the certain axis. The device may measure the impedance change of the cell by measuring the parameter changes of the first alternating magnetic field and the second alternating magnetic field.

The 30 degree angle at which the first plane and the second plane rotate is only an example, and the angle at which the first plane and the second plane rotate may be determined in various ways. For example, it may be desirable to measure the impedance change of the cell while rotating the first plane and the second plane finely by 1 degree.

Also, t=N and t=2N, which are the times when the first plane and the second plane rotate, are merely examples, and the time during which the first plane and the second plane rotate may be determined in various ways. A time interval in which the first plane and the second plane rotate may be an arbitrary time interval suitable for measuring the first alternating magnetic field and the second alternating magnetic field corresponding to each coil pair. For example, the time interval in which the first plane and the second plane rotate may be a time interval sufficient to measure waveform changes of the first alternating magnetic field and the second alternating magnetic field. The arbitrary time interval may be set by a user or determined by the controller 240.

The device may measure the impedance change of the cell at various angles using the parameter changes of the first alternating magnetic field and the second alternating magnetic field measured at various angles. The device may measure the change in the cell more stereoscopically by measuring the impedance change of the cell while rotating the first plane and the second plane by a predetermined angle.

Figure 6:
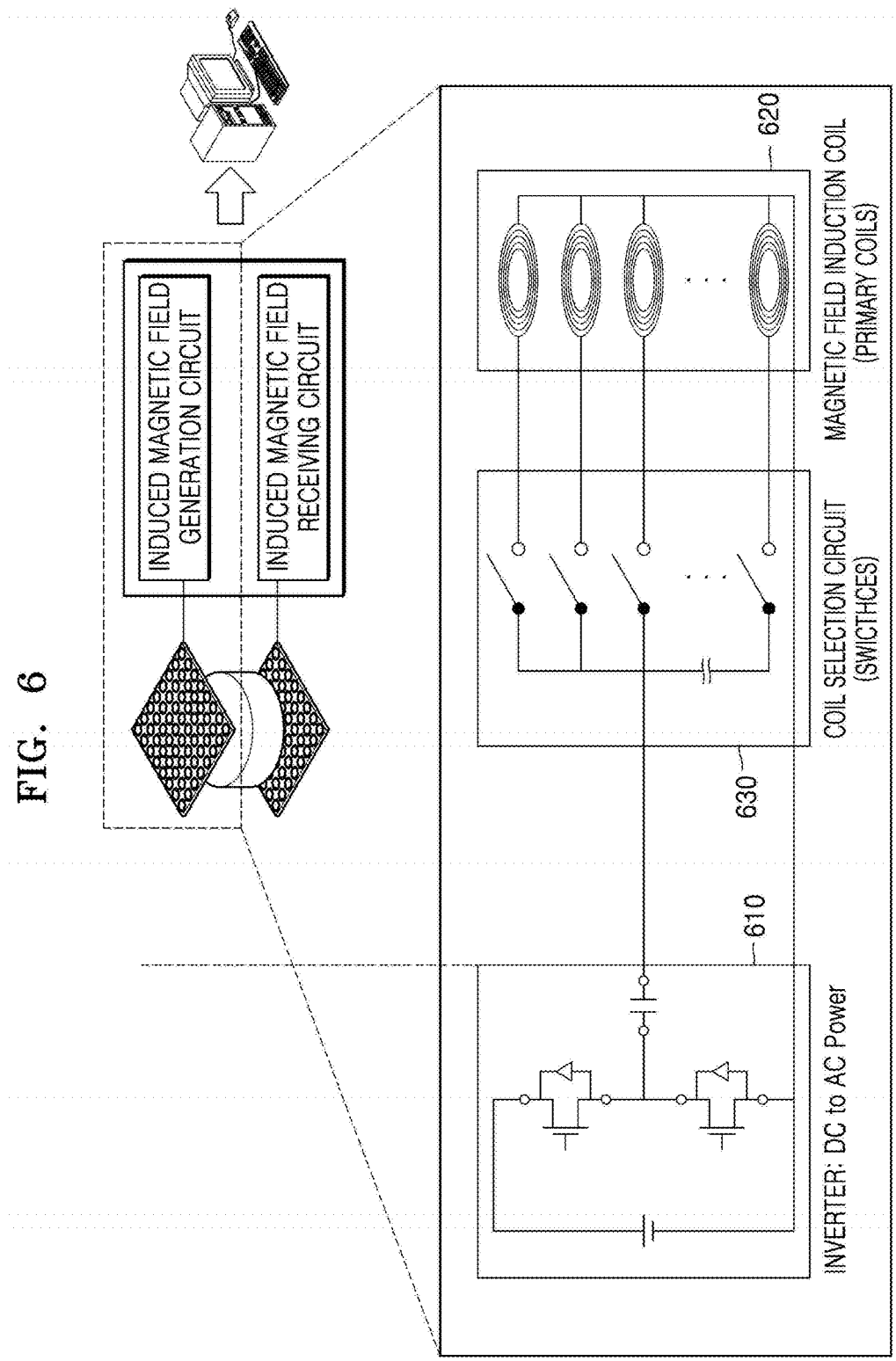
FIG. 6 is a diagram showing a configuration of an induced magnetic field generator according to an embodiment.

FIG. 6 is a diagram showing a configuration of an induced magnetic field generator according to an embodiment.

Referring to FIG. 6, the induced magnetic field generator may include an inverter 610, a plurality of primary coils 620, and a plurality of switches 630. The inverter 610 is an electrical device for converting DC into AC. The inverter 610 may convert DC to AC such that the plurality of primary coils 620 may generate an alternating magnetic field. The inverter 610 shown in FIG. 6 is merely an example, and various inverters that perform the same function may be used.

The plurality of primary coils 620 generate the alternating magnetic field. Each of the plurality of primary coils 620 may be controlled individually. The alternating magnetic field generated in each of the plurality of primary coils 620 may be received by a secondary coil after passing through the cell.

The plurality of switches 630 control the connection of the plurality of primary coils 620 with a power source. The plurality of switches 630 may respectively correspond to the plurality of primary coils 620. Thus, the plurality of primary coils 620 may be individually controlled by the plurality of switches 630, respectively.

Also, the induced magnetic field generator may further include at least one capacitor. When a frequency of the power source and a natural frequency determined by a capacitor and the coil are equal to each other, a resonance phenomenon occurs and thus current or voltage is maximized. This frequency is called a resonance frequency. The plurality of primary coils 620 may generate an alternating magnetic field having a frequency corresponding to the resonance frequency to increase the efficiency of power transmitted to secondary coils. When the efficiency of power transmitted to the secondary coils increases, it may be easy to measure parameter changes of the first alternating magnetic field and the second alternating magnetic field.

Figure 7:
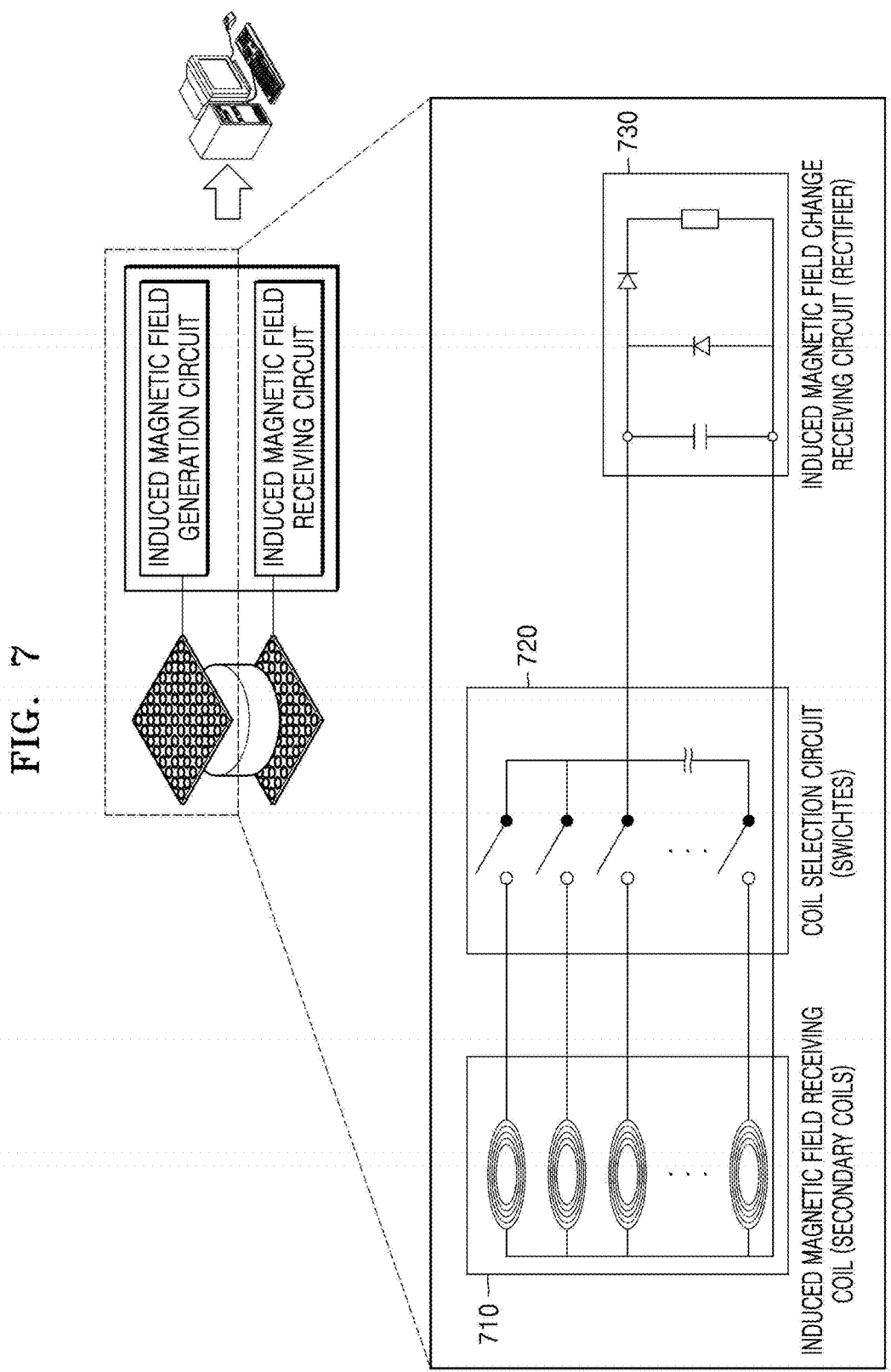
FIG. 7 is a diagram showing a configuration of an induced magnetic field receiver according to an embodiment.

FIG. 7 is a diagram showing a configuration of an induced magnetic field receiver according to an embodiment.

Referring to FIG. 7, the induced magnetic field receiver may include a plurality of secondary coils 710, a plurality of switches 720, and a rectifier 730. The induced magnetic field receiver detects parameter changes of an alternating magnetic field according to an impedance change of a cell located between a primary coil and a secondary coil.

The plurality of secondary coils 710 receive the alternating magnetic field. Each of the plurality of secondary coils 710 may be individually controlled and may receive the alternating magnetic field that passes through the cell.

The plurality of switches 720 control the connection of the plurality of secondary coils 710. The plurality of switches 720 may respectively correspond to the plurality of secondary coils 710. Thus, the plurality of secondary coils 710 may be individually controlled respectively by the plurality of switches 720.

The rectifier 730 is an electrical device for converting AC into DC. The rectifier 730 shown in FIG. 7 is merely an example, and various rectifiers performing the same function may be used.

Figure 8:
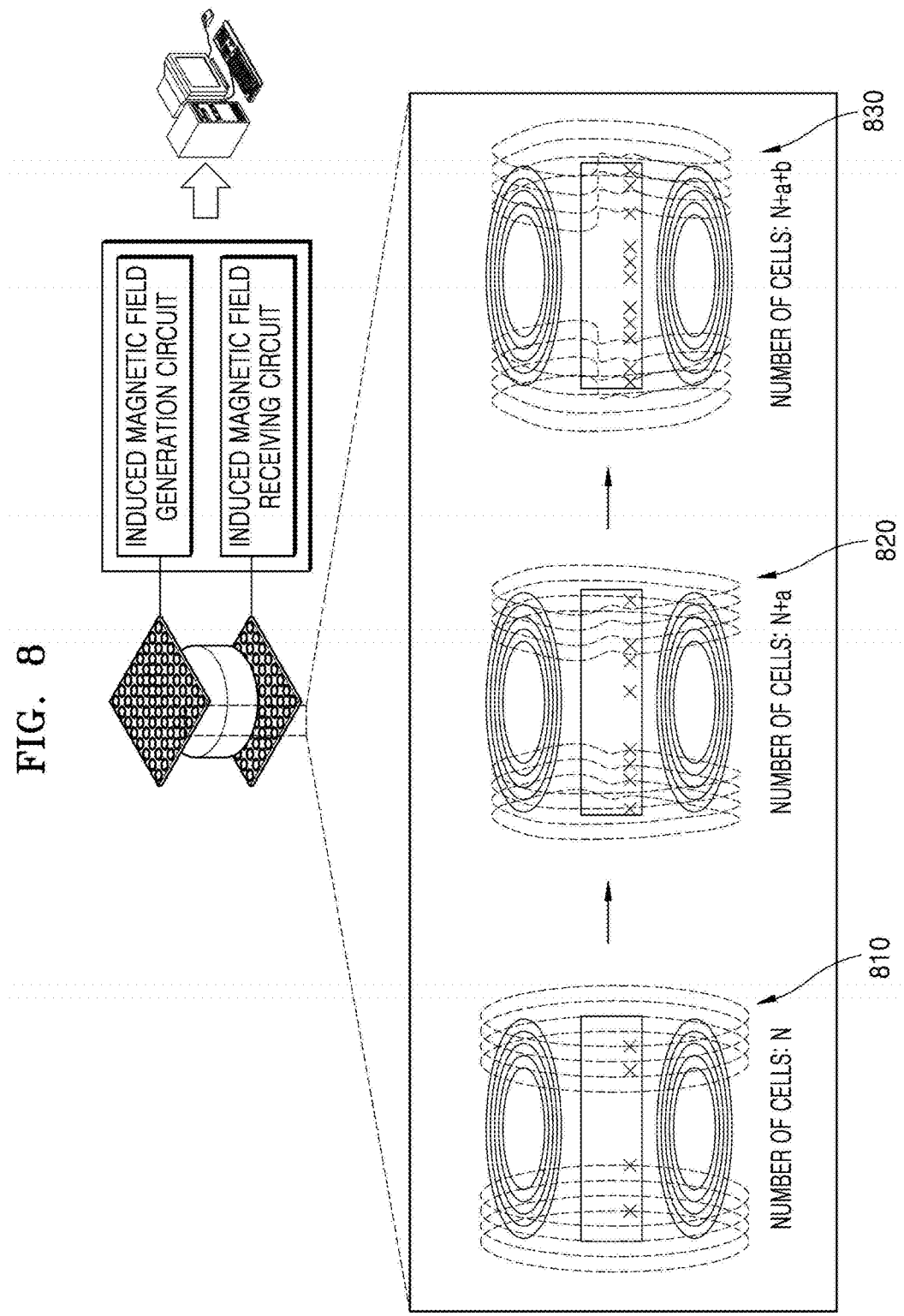
FIG. 8 illustrates induced magnetic field distribution charts with respect to a change in the number of cells according to an embodiment.

FIG. 8 illustrates induced magnetic field distribution charts 810, 820 and 830 with respect to a change in the number of cells according to an embodiment.

Referring to FIG. 8, the induced magnetic field distribution charts 810, 820 and 830 are shown when the number of cells in a chamber changes to N, N+a, and N+a+b. When the number of cells in the chamber is N, it may be an initial state of cell proliferation. The number of cells may not be so large as to affect an induced magnetic field distribution. Therefore, when the number of cells in the chamber is N, the induced magnetic field distribution chart 810 shows that the induced magnetic field is hardly affected by the cells.

When the number of cells in the chamber is N+a, the cell proliferation may be performed to some degree. It may be that the number of cells is large enough to have some effect on the induced magnetic field distribution. Therefore, when the number of cells in the chamber is N+a, the induced magnetic field distribution chart 820 shows that the induced magnetic field is affected to some extent by the cells.

When the number of cells in the chamber is N+a+b, the cell proliferation may be progressed a lot. The number of cells may be increased to such an extent as to greatly affect the induced magnetic field distribution. Therefore, when the number of cells in the chamber is N+a+b, the induced magnetic field distribution 830 shows that the induced magnetic field is greatly affected by the cells.

Thus, the number of cells affects the distribution of the induced magnetic field. As the number of cells increases, the impedance of all cells decreases and the distribution of the induced magnetic field changes. Therefore, when the change in the induced magnetic field is measured, impedance changes of the cells may be measured inversely.

In FIG. 8, an example of the change in the induced magnetic field distribution with respect to the number of cells is described, but the size of the cells or the type of the cells may also affect the induced magnetic field distribution. Therefore, when the change in the induced magnetic field is measured, a change in the size of the cells or the type of the cells may be measured inversely.

Figure 9:
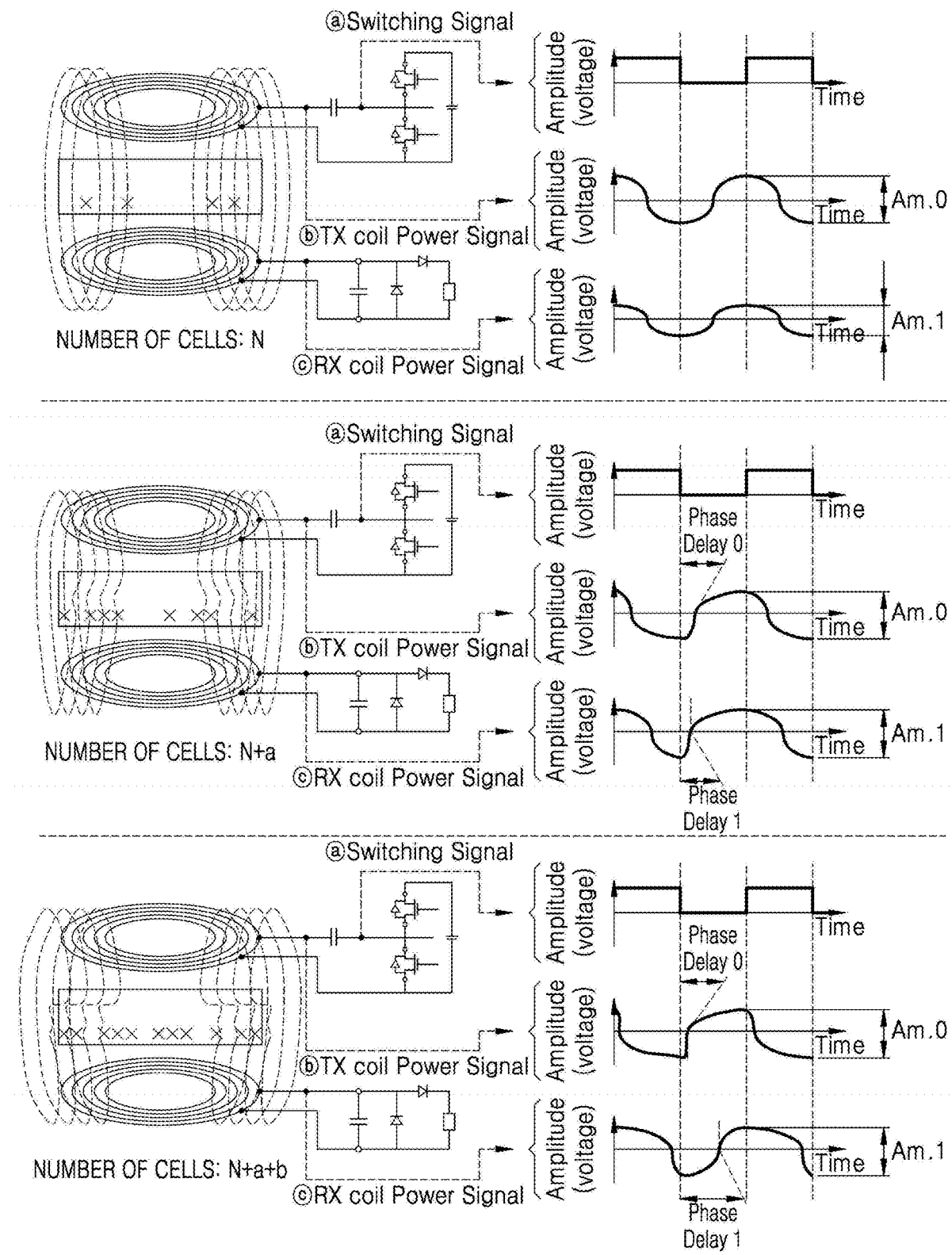
FIG. 9 illustrates changes in amplitude, phase, and waveform of an alternating current (AC) power signal with respect to a change in the number of cells according to an embodiment.

FIG. 9 illustrates changes in amplitude, phase, and waveform of an AC power signal with respect to a change in the number of cells according to an embodiment.

Referring to FIG. 9, it is shown how the amplitude, phase, and waveform of the AC power signal change with respect to the change in the number of cells. An induced magnetic field distribution chart with respect to the change in the number of cells in FIG. 9 may be explained in the same manner as in FIG. 8. The AC power signal may refer to power generated and induced in a plurality of primary coils and a plurality of secondary coils.

In FIG. 9, a TX coil power signal may refer to an AC power signal generated in the plurality of primary coils, and a RX coil power signal may refer to an AC power signal generated in the plurality of secondary coils. In FIG. 9, only AC power signals of arbitrary primary and secondary coils of the plurality of primary coils and the plurality of secondary coils are shown for convenience.

Referring to FIG. 9, it may be seen that as the number of cells in a chamber increases, a distribution of the induced magnetic field changes, and on the basis of the change, the amplitude, phase and waveform of the TX coil power signal and the RX coil power signal change. When the number of cells in the chamber increases, impedance of cells in the chamber changes. Impedance changes of the cells in the chamber cause a parameter change in the AC power signal generated and induced in the primary and secondary coils.

Therefore, the impedance changes of the cells may be inversely measured based on the amplitude, phase, and waveform of the TX coil power signal and the RX coil power signal. When the amplitude, phase, and waveform of the TX coil power signal and the RX coil power signal change greatly, the impedance changes of the cells are determined to be large. Further, when the amplitude, phase, and waveform of the TX coil power signal and the RX coil power signal change slightly, the impedance changes of the cells are determined to be small.

A device for measuring a change in a cell in real time may measure an impedance change of the cell based on AC power transmitted by a first alternating magnetic field and a second alternating magnetic field. The device for measuring the change in the cell in real time may measure a change in a first AC power signal generated in the plurality of primary coils and a change in a second AC power signal induced in the plurality of secondary coils. The device for measuring the change in the cell in real time may measure the impedance change of the cell based on the change of the first AC power signal and the change of the second AC power signal. The change in the first AC power signal and the change in the second AC power signal may be measured based on changes in amplitude, phase and shape, which are parameters of the first AC power signal and the second AC power signal.

Figure 10:
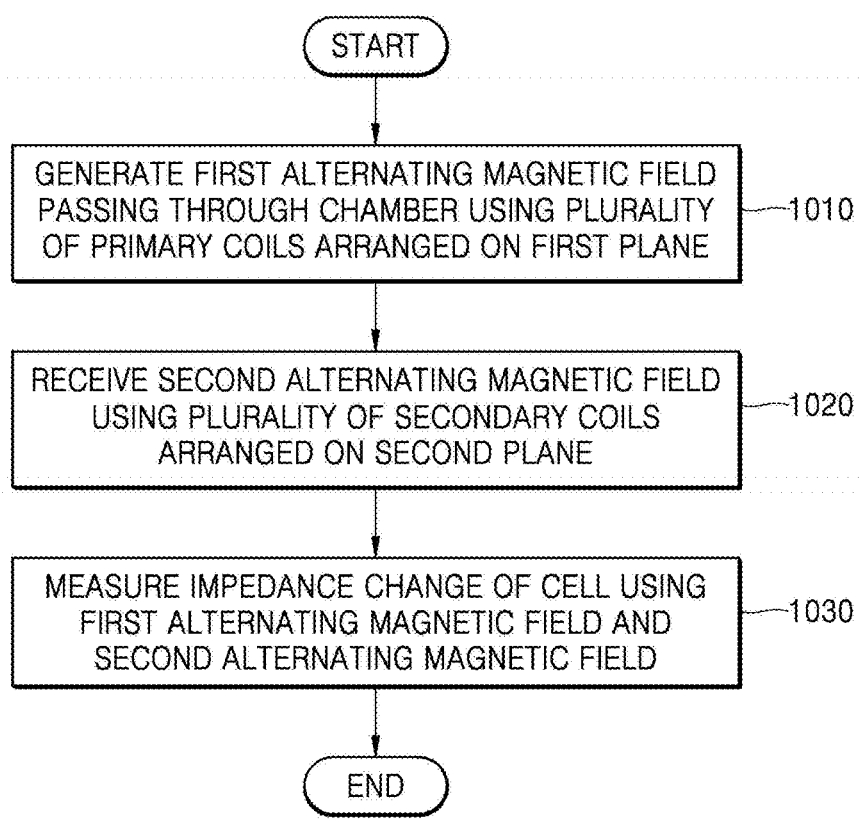
FIG. 10 is a diagram illustrating an example of a method of measuring a change in a cell in real time, according to an embodiment.

FIG. 10 is a diagram illustrating an example of a method of measuring a change in a cell in real time, according to an embodiment.

Referring to FIG. 10, a method of measuring the change in the cell in real time includes operations processed serially in time in the system 1 shown in FIG. 1 or the device 20 shown in FIG. 2. Therefore, it is understood that the descriptions provided above with respect to the system 1 of FIG. 1 or the device 20 of FIG. 2 apply to the method of measuring the change in the cell in real time in FIG. 10 even though omitted below.

A device for measuring the change in the cell in real time in operation 1010 may generate a first alternating magnetic field passing through a chamber in which the cell is arranged using a plurality of primary coils arranged in an array on a first plane. The device for measuring the change in the cell in real time may generate an alternating magnetic field by allowing AC to flow in the primary coil. A magnetic field generated by the current flowing in the primary coil is referred to as a first alternating magnetic field.

The plurality of primary coils may be arranged in an array on the first plane. For example, the plurality of primary coils may be arranged in the form of a one-dimensional array or a two-dimensional array. When the plurality of primary coils are arranged in the form of a two-dimensional array, the total n×m number of primary coils including n number vertically and m number horizontally may be arranged. Each of the plurality of primary coils may be individually controlled by the device for measuring the change in the cell in real time.

In operation 1020, the device for measuring the change in the cell in real time may receive a second alternating magnetic field using the plurality of secondary coils arranged on a second plane. The second alternating magnetic field is a magnetic field obtained by allowing the first alternating magnetic field to pass through the chamber.

The plurality of secondary coils may be arranged in the same form as the plurality of primary coils on the second plane parallel to the first plane. For example, when the plurality of primary coils are arranged in a two-dimensional array, the plurality of secondary coils may be arranged in a two-dimensional array. When the plurality of primary coils are arranged in an array of n number vertically and m number horizontally, the plurality of secondary coils may also be arranged in the same form. Because the plurality of primary coils and the plurality of secondary coils are arranged in the same form, a secondary coil at a position corresponding to an arbitrary primary coil may be determined.

In operation 1030, the device for measuring the change in the cell in real time may measure the impedance change of the cell using the first alternating magnetic field and the second alternating magnetic field. The device for measuring the change in the cell in real time may obtain change data of the first alternating magnetic field and the second alternating magnetic field and may analyze the obtained data to measure the impedance change of the cell.

The device for measuring the change in the cell in real time may measure the impedance change of the cell by measuring changes in parameters of the first alternating magnetic field and the second alternating magnetic field. The device for measuring the change in the cell in real time may measure the impedance change of the cell using at least one of an amplitude, a phase, and a waveform of the first alternating magnetic field and the second alternating magnetic field.

Also, the device for measuring the change in the cell in real time may measure the impedance change of the cell based on AC power transmitted by the first alternating magnetic field and the second alternating magnetic field. The device for measuring the change in the cell in real time may measure a change in the first AC power signal generated in the plurality of primary coils and a change in the second AC power signal induced in the plurality of secondary coils.

The device for measuring the change of the cell in real time may measure the impedance change of the cell based on the change of the first AC power signal and the change of the second AC power signal. The change in the first AC power signal and the change in the second AC power signal may be measured based on changes in amplitude, phase and shape, which are parameters of the first AC power signal and the second AC power signal.

The device for measuring the change of the cell in real time may determine a plurality of coil pairs using the plurality of primary coils and the plurality of secondary coils and may individually control an operation of each of the plurality of coil pairs. The coil pairs may include a first coil included in the plurality of primary coils and a second coil among the plurality of secondary coils disposed in a position corresponding to the first coil.

The device for measuring the change of the cell in real time may measure the first alternating magnetic field and the second alternating magnetic field corresponding to each coil pair by individually controlling the coil pairs. Therefore, the device for measuring the change of the cell in real time may measure the first alternating magnetic field and the second alternating magnetic field in a micro area range corresponding to each coil pair on the first plane.

The device for measuring the change of the cell in real time may finely measure the impedance change of the cell using the first alternating magnetic field and the second alternating magnetic field measured within the micro area range. The device for measuring the change of the cell in real time may perform a more precise analysis operation by observing a cell change of a micro part in the chamber.

The device for measuring the change of the cell in real time may sequentially control each of the plurality of coil pairs according to a predetermined time interval. For example, it is supposed that the plurality of primary coils and secondary coils are arranged in the form of a two-dimensional array of n number horizontally and m number vertically. When positions of the coils are represented by a matrix, the coil pairs arranged in the two-dimensional array may be represented by the matrix of the total n×m number of (1, 1), (1, 2), . . . , (n, m). The device for measuring the change of the cell in real time may control the plurality of coil pairs in the order of (1, 1), (1, 2), . . . , (n, m).

The predetermined time interval may be an arbitrary time interval suitable for measuring the first alternating magnetic field and the second alternating magnetic field corresponding to each coil pair. For example, the predetermined time interval may be a time interval sufficient to measure waveform changes of the first alternating magnetic field and the second alternating magnetic field Also, the device for measuring the change of the cell in real time may measure the impedance change of the cell while rotating the first plane and the second plane by a predetermined angle. The device for measuring the change of the cell in real time may measure parameter changes of the first alternating magnetic field and the second alternating magnetic field while rotating the first plane and the second plane by a predetermined angle.

The device for measuring the change of the cell in real time may measure the impedance change of the cell at various angles by using the measured parameter changes of the first alternating magnetic field and the second alternating magnetic field. The device for measuring the change of the cell in real time may measure the change of the cell more stereoscopically by measuring the impedance change of the cell while rotating the first plane and the second plane by a predetermined angle.

The device for measuring the change of the cell in real time may determine a change in at least one of number, size, and type of cells based on the impedance change of the cell. In an example, the device for measuring the change of the cell in real time may determine the change in the number of cells based on the impedance change of the cell. For example, when the impedance of the cell measured by the device for measuring the change of the cell in real time gradually decreases, the device for measuring the change of the cell in real time may determine that the number of cells is gradually increasing. In this case, the cells in the chamber may be proliferating.

In another example, the device for measuring the change of the cell in real time may determine the change in the size of the cell based on the impedance change of the cell. For example, when the impedance of the cell measured by the device for measuring the change of the cell in real time decreases gradually, the device for measuring the change of the cell in real time may determine that the size of the cell is gradually increasing. In order for the device for measuring the change of the cell in real time to determine the change in the size of the cell based on the impedance change of the cell, the number of cells to be measured must be maintained to be constant.

In another example, the device for measuring the change of the cell in real time may determine the change in the type of the cell based on the impedance change of the cell. Different types of cells have different impedance distributions. Therefore, when an experiment is performed under the same condition such as the number of cells, the type of the cell may be inferred from an impedance distribution. The device for measuring the change of the cell in real time may determine the type of the cell based on the impedance change of the cell measured using the first alternating magnetic field and the second alternating magnetic field.

Figure 11:
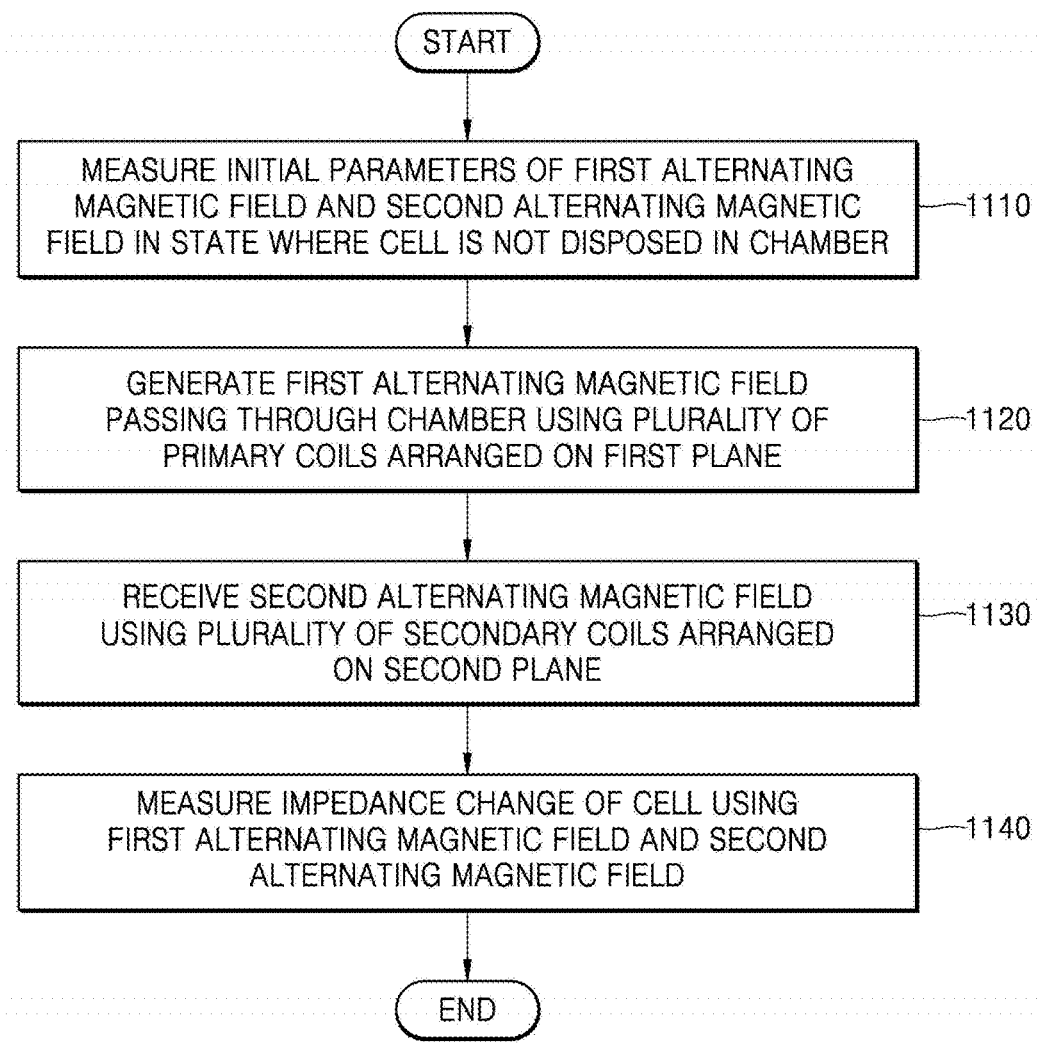
FIG. 11 is a diagram illustrating another example of a method of measuring a change in a cell in real time, according to an embodiment.

FIG. 11 is a diagram illustrating another example of a method of measuring a change in a cell in real time, according to an embodiment.

Referring to FIG. 11, in operation 1110, a device for measuring a change of the cell in real time may measure initial parameters of a first alternating magnetic field and a second alternating magnetic field in a state where the cell is not disposed in a chamber. In order to measure an impedance change of the cell using parameter changes of the first alternating magnetic field and the second alternating magnetic field, the reference of the parameters of the first alternating magnetic field and the second alternating magnetic field may be required. Therefore, the device for measuring the change of the cell in real time may measure the initial parameters of the first alternating magnetic field and the second alternating magnetic field in the state where the cell is not disposed in the chamber.

In operation 1120, the device for measuring the change of the cell in real time may generate the first alternating magnetic field passing through the chamber in which the cell is disposed using a plurality of primary coils arranged in an array on a first plane. The device for measuring the change of the cell in real time may generate an alternating magnetic field by allowing AC to flow in the primary coil. The magnetic field generated by the current flowing in the primary coil is referred to as the first alternating magnetic field. Operation 1120 of FIG. 11 may be the same step as operation 1010 of FIG. 10, and thus a detailed description of operation 1120 will be omitted below.

In operation 1130, the device for measuring the change of the cell in real time may receive the second alternating magnetic field using a plurality of secondary coils arranged on a second plane. The second alternating magnetic field is a magnetic field obtained by allowing the first alternating magnetic field to pass through the chamber. Operation 1130 of FIG. 11 may be the same step as operation 1020 of FIG. 10, and thus a detailed description of operation 1130 will be omitted below.

In operation 1140, the device for measuring the change of the cell in real time may measure the impedance change of the cell using the first alternating magnetic field and the second alternating magnetic field. The device for measuring the change of the cell in real time may obtain change data of the first alternating magnetic field and the second alternating magnetic field and may analyze the obtained data to measure the impedance change of the cell.

The device for measuring the change of the cell in real time may measure the impedance change of the cell by measuring changes in parameters of the first alternating magnetic field and the second alternating magnetic field. At this time, the changes in the parameters of the first alternating magnetic field and the second alternating magnetic field may be measured using the initial parameters measured in operation 1110. The device for measuring the change of the cell in real time may measure the impedance change of the cell using at least one of an amplitude, a phase, and a waveform of the first alternating magnetic field and the second alternating magnetic field.

Also, the device for measuring the change of the cell in real time may measure the impedance change of the cell based on AC power transmitted by the first alternating magnetic field and the second alternating magnetic field. The device for measuring the change of the cell in real time may measure a change in a first AC power signal generated in the plurality of primary coils and a change in a second AC power signal induced in the plurality of secondary coils.

The device for measuring the change of the cell in real time may measure the impedance change of the cell based on the change of the first AC power signal and the change of the second AC power signal. The change in the first AC power signal and the change in the second AC power signal may be measured based on changes in amplitude, phase and shape, which are parameters of the first AC power signal and the second AC power signal. At this time, the changes in the parameters of the first AC power signal and the second AC power signal may be measured using the initial parameters measured in operation 1110.

Operation 1140 of FIG. 11 may be the same step as operation 1030 of FIG. 10, and thus a detailed description of operation 1140 will be omitted below.

The method of operating a device for measuring a change in a cell in real time may be recorded on a computer-readable recording medium having recorded thereon one or more programs including instructions for performing the method. Examples of the computer-readable recording medium may include magnetic media such as a hard disk, a floppy disk, and magnetic tape, optical media such as CD-ROM and digital video disc (DVD), magneto-optical media such as a floptical disk, and a hardware apparatus, such as ROM, RAM, and flash memory, specifically configured to store and execute program instructions. Examples of the program instructions may include not only machine language code generated by a compiler but also high-level language code executable by a computer by using an interpreter or the like.

It should be understood that the embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

The invention claimed is:

1. A device for measuring a change in a cell in real time, the device comprising:
a chamber in which the cell is arranged;
an induced magnetic field generator configured to generate a first alternating magnetic field passing through the chamber using a plurality of primary coils arranged on a first plane;
an induced magnetic field receiver configured to receive a second alternating magnetic field using a plurality of secondary coils arranged on a second plane; and
a controller configured to control the induced magnetic field generator and the induced magnetic field receiver and measure an impedance change of the cell using the first alternating magnetic field and the second alternating magnetic field,
wherein the second alternating magnetic field is a magnetic field obtained by allowing the first alternating magnetic field to pass through the chamber.

2. The device of claim 1, wherein the plurality of primary coils are arranged in an array on the first plane and the plurality of secondary coils are arranged on the second plane parallel to the first plane in the same form as the plurality of primary coils.

3. The device of claim 1, wherein the controller is configured to determine a plurality of coil pairs using the plurality of primary coils and the plurality of secondary coils and individually control an operation of each of the plurality of coil pairs,
wherein the plurality of coil pairs comprise a first coil included in the plurality of primary coils and a second coil among the plurality of secondary coils disposed in a position corresponding to the first coil.

4. The device of claim 1, wherein the controller is configured to sequentially control each of a plurality of coil pairs according to a predetermined time interval.

5. The device of claim 1, wherein the controller is configured to measure the impedance change of the cell while rotating the first plane and the second plane by a predetermined angle.

6. The device of claim 1, wherein the controller is configured to measure the impedance change of the cell by measuring changes in parameters of the first alternating magnetic field and the second alternating magnetic field.

7. The device of claim 1, wherein the controller is configured to measure initial parameters of the first alternating magnetic field and the second alternating magnetic field in a state where the cell is not disposed in the chamber and measure the impedance change of the cell based on the measured initial parameters.

8. The device of claim 1, wherein the controller is configured to measure the impedance change of the cell using at least one of an amplitude, a phase, and a waveform of the first alternating magnetic field and the second alternating magnetic field.

9. The device of claim 1, wherein the controller is configured to determine a change in at least one of a number, a size, and a type of the cell based on the impedance change of the cell.

10. The device of claim 1, wherein the induced magnetic field generator comprises an inverter configured to convert a direct current (DC) into an alternating current (AC), the plurality of primary coils, and a plurality of switches corresponding to the plurality of primary coils, respectively.

11. The method of claim 1, wherein the induced magnetic field receiver comprises the plurality of secondary coils, a plurality of switches corresponding to the plurality of secondary coils, respectively, and a rectifier configured to convert alternating current (AC) power into direct current (DC) power.

12. A method of measuring a change in a cell in real time, the method comprising:
generating a first alternating magnetic field passing through a chamber in which the cell is disposed using a plurality of primary coils arranged on a first plane;
receiving a second alternating magnetic field using a plurality of secondary coils arranged on a second plane; and
measuring an impedance change of the cell using the first alternating magnetic field and the second alternating magnetic field,
wherein the second alternating magnetic field is a magnetic field obtained by allowing the first alternating magnetic field to pass through the chamber.

13. The method of claim 12, wherein the plurality of primary coils are arranged in an array on the first plane and the plurality of secondary coils are arranged on the second plane parallel to the first plane in the same form as the plurality of primary coils.

14. The method of claim 12, further comprising:
determining a plurality of coil pairs using the plurality of primary coils and the plurality of secondary coils; and
individually controlling an operation of each of the plurality of coil pairs,
wherein the plurality of coil pairs comprise a first coil included in the plurality of primary coils and a second coil among the plurality of secondary coils disposed in a position corresponding to the first coil.

15. The method of claim 14, wherein the controlling comprises sequentially controlling each of the plurality of coil pairs according to a predetermined time interval.

16. The method of claim 12, further comprising measuring the impedance change of the cell while rotating the first plane and the second plane by a predetermined angle.

17. The method of claim 12, further comprising measuring the impedance change of the cell by measuring changes in parameters of the first alternating magnetic field and the second alternating magnetic field.

18. The method of claim 12, further comprising measuring initial parameters of the first alternating magnetic field and the second alternating magnetic field in a state where the cell is not disposed in the chamber and measuring the impedance change of the cell based on the measured initial parameters.

19. The method of claim 12, wherein the measuring comprises measuring the impedance change of the cell using at least one of an amplitude, a phase, and a waveform of the first alternating magnetic field and the second alternating magnetic field.

20. The method of claim 12, further comprising determining a change in at least one of a number, a size, and a type of the cell based on the impedance change of the cell.

21. A non-transitory computer-readable recording medium having recorded thereon one or more programs comprising instructions for executing the method of claim 12.

* * * * *